US011523819B2

(12) United States Patent
Jung

(10) Patent No.: US 11,523,819 B2
(45) Date of Patent: Dec. 13, 2022

(54) SUTURING THREAD FOR FACELIFT AND BODY LIFT

(71) Applicant: Jetema Co., Ltd., Seoul (KR)

(72) Inventor: Young Choon Jung, Seongnam-si (KR)

(73) Assignee: JETEMA CO., LTD., Seoul (KR)

( * ) Notice: Subject to any disclaimer, the term of this patent is extended or adjusted under 35 U.S.C. 154(b) by 155 days.

(21) Appl. No.: 16/073,219

(22) PCT Filed: Jan. 24, 2017

(86) PCT No.: PCT/KR2017/000831
§ 371 (c)(1),
(2) Date: Jul. 26, 2018

(87) PCT Pub. No.: WO2017/131416
PCT Pub. Date: Aug. 3, 2017

(65) Prior Publication Data
US 2019/0046184 A1 Feb. 14, 2019

(30) Foreign Application Priority Data
Jan. 28, 2016 (KR) .................. 10-2016-0010922

(51) Int. Cl.
*A61L 17/04* (2006.01)
*A61B 17/00* (2006.01)
*A61B 17/06* (2006.01)
*A61F 2/00* (2006.01)
(Continued)

(52) U.S. Cl.
CPC ........ *A61B 17/06166* (2013.01); *A61B 17/06* (2013.01); *A61F 2/00* (2013.01); *A61L 17/04* (2013.01); *A61L 17/10* (2013.01); *A61L 33/06* (2013.01); *A61B 2017/00004* (2013.01); *A61B 2017/00792* (2013.01); *A61B 2017/06176* (2013.01)

(58) Field of Classification Search
CPC .............. A61B 17/06166; A61B 17/06; A61B 2017/00004; A61B 2017/00792; A61B 2017/06176; A61F 2/00; A61L 17/04; A61L 17/10; A61L 33/06
See application file for complete search history.

(56) References Cited

U.S. PATENT DOCUMENTS 6,241,747 B1 * 6/2001 Ruff ................. A61B 17/06109
411/456
8,226,684 B2 * 7/2012 Nawrocki ........ A61B 17/06166
606/228
(Continued)

FOREIGN PATENT DOCUMENTS

CN 1630537 A 6/2005
CN 103251433 A 8/2013
(Continued)

*Primary Examiner* — Jing Rui Ou
(74) *Attorney, Agent, or Firm* — Hamilton, Brook, Smith & Reynolds, P.C.

(57) ABSTRACT

The present invention relates to a suturing thread for providing a more efficient lift procedure, and provides a suturing thread for a facelift and a body lift, wherein the suturing thread is made of a polymer material and has a plurality of conical protrusions or a plurality of funneled protrusions formed on an outer circumferential surface of a main thread of the suturing thread.

15 Claims, 5 Drawing Sheets

(51) Int. Cl.
*A61L 17/10* (2006.01)
*A61L 33/06* (2006.01)

(56) References Cited

U.S. PATENT DOCUMENTS

| | | | | |
|---|---|---|---|---|
| 2003/0149447 | A1* | 8/2003 | Morency | A61B 17/06166 606/228 |
| 2005/0261737 | A1* | 11/2005 | Sakura | A61B 17/0482 606/215 |
| 2006/0079935 | A1* | 4/2006 | Kolster | A61B 17/06 606/228 |
| 2007/0005110 | A1* | 1/2007 | Collier | A61F 2/2409 606/228 |
| 2007/0038249 | A1* | 2/2007 | Kolster | A61B 17/06166 606/228 |
| 2007/0239207 | A1* | 10/2007 | Beramendi | A61L 17/00 606/228 |
| 2008/0004490 | A1* | 1/2008 | Bosley | A61B 17/06109 600/37 |
| 2010/0160961 | A1* | 6/2010 | Nawrocki | A61B 17/06166 606/228 |
| 2012/0101524 | A1* | 4/2012 | Bennett | A61B 17/0401 606/232 |
| 2014/0222071 | A1* | 8/2014 | Perkins | A61B 17/06166 606/228 |

FOREIGN PATENT DOCUMENTS

| | | |
|---|---|---|
| EP | 3409213 | 12/2018 |
| JP | 2005-532848 A | 11/2005 |
| JP | 2010-500102 A | 2/2007 |
| JP | 2011-518588 A | 10/2009 |
| KR | 10-2005-0108494 A | 11/2005 |
| KR | 10-2006-0059142 A | 6/2006 |
| KR | 10-2009-0035692 A | 4/2009 |
| KR | 10-2011-0003532 A | 1/2011 |
| KR | 10-1057376 B1 | 8/2011 |
| KR | 10-1057377 B1 | 8/2011 |
| KR | 10-1455683 B1 | 11/2014 |
| KR | 10-1490613 B1 | 2/2015 |
| WO | 2009129251 A2 | 10/2009 |

* cited by examiner

SUTURING THREAD FOR FACELIFT AND BODY LIFT

This application is the U.S. National Stage of International Application No. PCT/KR2017/000831, filed Jan. 24, 2017, which designates the U.S., published in Korean, and claims priority under 35 U.S.C. § 119 or 365(c) to Korean Application No. 10-2016-0010922, filed Jan. 28, 2016. The entire teachings of the above applications are incorporated herein by reference.

TECHNICAL FIELD

The present invention relates to a suturing thread, specifically, a suturing thread for face lift and body lift.

BACKGROUND ART

Suturing thread is a thread for stitching a wound during surgery. Suturing thread is generally categorized into those consisting of a biodegradable or absorbable polymer material such as collagen or PLGA [poly(lactic-co-glycolic) acid], which are degraded in a living body and get absorbed by a skin over time, and those consisting of a non-biodegradable polymer material which needs to be removed after a procedure. In recent years, due to the biocompatibility and convenience in procedure, those consisting of a biodegradable polymer are used more commonly. Furthermore, in case of a suturing thread consisting of such biodegradable polymer material, it is recently used also for face lift to pull and stretch a loose skin. To fix the skin after pulling a suturing thread inserted under a skin, a suturing thread having barbs, knots, or protrusions formed thereon has been produced and used. With regard to such suturing thread having barbed or protruded structure, there are Korean Patent Registration No. 1057376 which relates to a method for producing a suturing thread characterized in that an injection-molded suturing thread forming body is stretched to a solid state within a range between glass transition temperature and melting point of a bioabsorbable polymer constituting the thread forming body and the stretched suturing thread is subjected to a heat treatment, and Korean Patent Registration No. 1455683 which relates to a suturing thread having cogs formed in two directions. However, for those barbs, knots, or protrusions, although partially automated facilities are available for the production, they are mainly produced by handwork like scoring on a smooth surface of a suturing thread to form a cogged structure or forming knots, or the like, and thus high production cost remains as a problem. Furthermore, in case of a suturing thread made of a biodegradable polymer material on which barbs or protrusions are formed, the barb or protrusion part has smaller thickness than a main body of the suturing thread, and thus there is a problem that the barb or protrusion part is degraded before biodegradation of a main body of the suturing thread in skin tissue, yielding loosening of the lifted part even before the skin is fixed.

Accordingly, there has been a need for developing a suturing thread for more effective face lift and body lift, in which barbs or protrusions substantially playing the role of lifting as they undergo biodegradation after fixing of a lifted skin can be maintained for even longer period of time.

SUMMARY OF THE INVENTION

Problems to be Solved by the Invention

Object of the present invention is to provide a novel suturing thread for face lift and body lift which can inhibit the degradation of barbs or protrusions before lifted skin is fixed.

Another object of the present invention is to improve the phenomena as follows: as a suturing thread for face lift and body lift of a prior art is broken inside a tissue according to movement of facial muscles, 1) binding to an anchor point present at the end or center part is disconnected to yield a lower lifting effect, 2) lifting tension is lost in accordance with a conversion in pulling vector that is generated by unstraight insertion of a thread, and 3) due to breakage of a thread, cogs formed in two directions become to have directivity of single direction and pushed away to the outside of a tissue.

Still another object of the present invention is to enable one cog or one protrusion to effectively support as many tissues as possible by increasing the surface area of a cog or a protrusion, which has a short duration of having the lifting effect as object of a procedure since the absorption rate of cogs of a lifting thread is higher than the absorption rate of a suturing thread, and has weak tension due to small application area, in which those problems have remained as a limitation caused by a small surface area of a cog of a prior art.

Means for Solving Problem

According to one aspect of the present invention, provided is a suturing thread for face lift and body lift made of a polymer or gold with a plurality of protrusions formed on an outer circumferential surface of a main thread of the suturing thread in which the protrusion has a stereo structure of cone, polygonal cone, truncated cone, modified polygonal cone, truncated polygonal cone, modified truncated polygonal cone, cylinder, modified cylinder, polygonal cylinder, or modified polygonal cylinder that are formed to have a radially symmetric structure around a main thread of the suturing thread, or has a funnel shape in which a part or whole of the space excluding the outer circumferential surface of the stereo structure and a main thread part of the suturing thread present inside is empty, and the plurality of protrusions is symmetrically arranged such that their vertices can face each other with respect to the center of the suturing thread.

According to another example of the present invention, provided is a suturing thread for face lift and body lift made of a polymer or gold with a plurality of paired protrusions or protrusion units formed on an outer circumferential surface of a main thread of the suturing thread in which the protrusion has a stereo structure of cone, polygonal cone, truncated cone, modified polygonal cone, truncated polygonal cone, modified truncated polygonal cone, cylinder, modified cylinder, polygonal cylinder, or modified polygonal cylinder that are formed to have a radially symmetric structure around a main thread of the suturing thread, or has a funnel shape in which a part or whole of the space excluding the outer circumferential surface of the stereo structure and a main thread part of the suturing thread present inside is empty.

With regard to a plurality of the paired protrusions or protrusion units in the suturing thread for face lift and body lift, the pair is formed such that the bottom surfaces or vertices of the protrusions can face each other so that one pair of protrusions or protrusion units can exert simultaneously the lifting function and anchoring function.

In addition, with regard to the suturing thread for face lift and body lift according to the present invention, the protrusion unit may have not only the symmetric protrusions, i.e., a bobbin shape (- ->-<- -) in which the bottom surfaces or vertices of the protrusions face each other or a spear shape (- -<->- -) with sharp end, but also an asymmetric shape (e.g., -<<->- -, - -<-<->- -, - ->>-<-, or - ->-><- -) in which number of protrusions is higher on one side.

According to the pair of protrusions or one protrusion unit described above, an individual protrusion pair or protrusion unit works as one lifting unit and also can simultaneously play the role of a fixing body (i.e., anchor), and therefore, even when a specific part of a suturing thread is broken or melt away, it can still play the role of lifting.

The suturing thread for face lift and body lift according to one example of the present invention can be produced by injection molding using a mold, cutting process using a lathe, variable extrusion molding using an extruder provided with variable nozzle, or heating-compression solid phase molding in which molding is carried out at temperature condition that the temperature is between the glass transition temperature and melting point. However, it is preferably produced by a variable cross-section extrusion process using a variable cross-section extruder provided with variable nozzle.

Effect of the Invention

The suturing thread for face lift and body lift according to one example of the present invention can not only solve the problem of losing the lifting effect due to the degradation of barbs or protrusions before skin is fixed as it enables forming of protrusions having certain thickness or higher, which can fix skin tissues, all over the outer circumferential surface of the suturing thread, but also can exert tension over the entire skin tissues near the suturing thread, and thus a more stable lifting effect can be exhibited. In this regard, it is needless to say that the scope of the present invention is not limited to those effects.

Furthermore, because the individual protrusion or protrusion unit of the suturing thread for face lift and body lift according to the examples of the present invention plays the role of an anchoring point while simultaneously providing the lifting effect, the individual protrusion can maintain the lifting effect even when the thread is broken due to the property of a thread described above, and also can simultaneously have enhanced maintenance period after the procedure and enhanced procedural effect as the migration inside a tissue is minimized. In this regard, it is needless to say that the scope of the present invention is not limited to those effects.

BEST MODES FOR CARRYING OUT THE INVENTION

Figure 1:
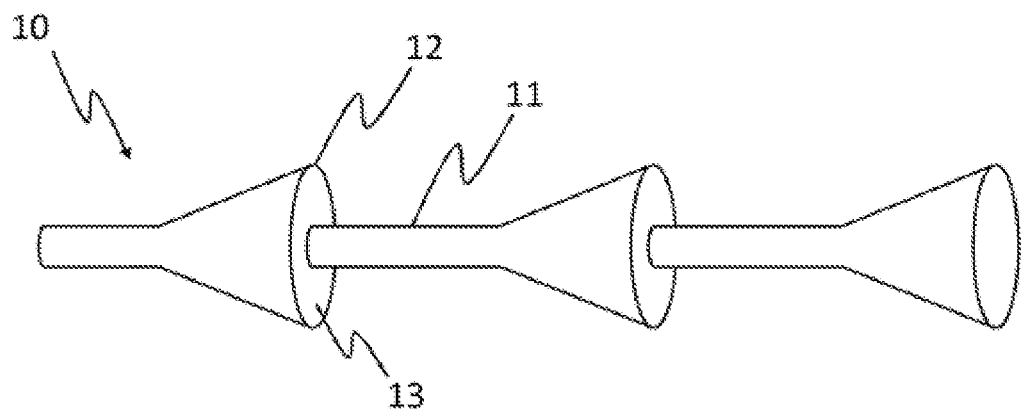
FIG. 1 is a schematic drawing briefly illustrating the structure of the suturing thread for face lift and body lift according to one example of the present invention.

According to one aspect of the present invention, provided is a suturing thread for face lift and body lift made of a polymer or gold with a plurality of protrusions formed on an outer circumferential surface of a main thread of the suturing thread in which the protrusion has a stereo structure of cone, polygonal cone, truncated cone, modified polygonal cone, truncated polygonal cone, modified truncated polygonal cone, cylinder, modified cylinder, polygonal cylinder, or modified polygonal cylinder that are formed to have a radially symmetric structure around a main thread of the suturing thread, or has a funnel shape in which a part or whole of the space excluding the outer circumferential surface of the stereo structure and a main thread part of the suturing thread present inside is empty, and the plurality of protrusions is symmetrically arranged such that their vertices can face each other with respect to the center of the suturing thread.

According to another example of the present invention, provided is a suturing thread for face lift and body lift made of a polymer or gold with a plurality of paired protrusions or protrusion units formed on an outer circumferential surface of a main thread of the suturing thread in which the protrusion has a stereo structure of cone, polygonal cone, truncated cone, modified polygonal cone, truncated polygonal cone, modified truncated polygonal cone, cylinder, modified cylinder, polygonal cylinder, or modified polygonal cylinder that are formed to have a radially symmetric structure around a main thread of the suturing thread, or has a funnel shape in which a part or whole of the space excluding the outer circumferential surface of the stereo structure and a main thread part of the suturing thread present inside is empty.

With regard to a plurality of the paired protrusions or protrusion units in the suturing thread for face lift and body lift, the pair is formed such that the bottom surfaces or vertices of the protrusions can face each other so that one pair of protrusions or protrusion units can exert simultaneously the lifting function and anchoring function.

With regard to the suturing thread for face lift and body lift according to the present invention, the protrusion units may have not only the symmetric protrusions, i.e., a bobbin shape (- ->-<- -) in which the bottom surfaces or vertices of the protrusions face each other or a spear shape (- -<->- -) with sharp end, but also an asymmetric shape (e.g., -<<->-  -, - -<-<->- -, - ->>-<-, or - ->-><- -) in which number of protrusions is higher on one side.

With regard to the suturing thread for face lift and body lift, the generatrix of the protrusion can be formed at an angle of 20° to 60° relative to the center axis of the main thread of a suturing thread and the protrusion may have a shape in which the bottom surface has a flat shape or a concaved shape having a depression in imaginary vertex direction of the protrusion. Similarly, when a part or whole of the inside excluding the outer wall of a protrusion and the main thread part of a suturing thread is empty (such case is referred to as a 'funnel-shaped protrusion' for the sake of convenience), thickness of the outer wall of the funnel shape can be at least 30% to 90% of the main body of a suturing thread. In this case, the funnel-shaped protrusion may have a shape in which at least one radial dent is formed and split.

With regard to the suturing thread for face lift and body lift, the modified polygonal cone, modified truncated polygonal cone, or modified polygonal cylinder means a shape in which the lateral surface is either recessed or protruded instead of having a flat surface. The modified cylinder shape means a shape in which the lateral surface has a recessed dent or a protruding part instead of a completely circular shape.

With regard to the suturing thread for face lift and body lift, the polymer can be either a non-absorbable polymer or a absorbable polymer, and the non-absorbable polymer can be PET (polyenthylene terephthalate), nylon, polyamide, PVDF (polyvinyldene fluoride), or polypropylene, and the absorbable polymer can be polydioxanone, polymer of lactic acid (L-lactide) (i.e., polylactic acid), polymer of glycolic acid (glycolide) (i.e., polyglycolic acid), copolymer of lactic acid and glycolic acid (glycolide) [i.e., poly(lactic-co-glycolic acid)], or poly dioxane, or it can be any one selected from polymers in which lactic acid (L-lactide), glycolic acid (glycolide), or a copolymer thereof is blended with caplolactone or trimethylene carbonate. The suturing thread can be also made of gold.

With regard to the suturing thread for face lift and body lift, a plurality of paired protrusions may have a symmetry such that vertices or bottom surfaces of the protrusions can face each other.

With regard to the suturing thread for face lift and body lift, the protrusion unit may be formed such that a plurality of the protrusions in one direction and a single protrusion or a plurality of the protrusions in the opposite direction are alternately arranged. In that case, it can be symmetric form in which number of the protrusions in one direction is the same as number of the protrusions in the opposite direction, or asymmetric form in which number of the protrusions in one direction is different from number of the protrusions in the opposite direction.

In addition, with regard to the suturing thread for face lift and body lift, the protrusion or protrusion unit may be formed either in one direction or two directions, and the protrusion or protrusion unit may form a pair such that the vertices or bottom surfaces of the protrusions can face each other.

More specifically, the protrusion can be formed in two directions such that an imaginary vertex, at which extended generatrix lines meet each other inside the main thread of a suturing thread, leans toward both ends, or the protrusion can be formed in two directions such that an imaginary vertex leans toward the center part.

Furthermore, the protrusion can have a Jang-gu (i.e., hourglass-shaped and double-headed Korean drum) shape with circular cross-section or a Jang-gu shape with polygonal cross-section in which the generatrix is connected at both ends at an angle of 20° to 60° relative to the center axis of the main thread of a suturing thread and the middle part is, in the same line as the main thread, thicker than the main thread.

With regard to the suturing thread for face lift and body lift, the protrusion or protrusion unit may be formed in one direction or two directions.

With regard to the suturing thread for face lift and body lift, the bottom surface of the protrusion may have a circular shape, an oval shape, a polygonal shape, or a modified polygonal shape.

With regard to the suturing thread for face lift and body lift, the continuously-arranged protrusions may be formed with either a regular size or an irregular size.

With regard to the suturing thread for face lift and body lift, the continuously-arranged protrusions may be formed with either a regular shape or an irregular shape.

With regard to the suturing thread for face lift and body lift, at least one cog may be formed either regularly or irregularly on a protrusion and/or a main thread of the suturing thread.

With regard to the suturing thread for face lift and body lift, the vertices or bottom surfaces of the protrusions or protrusion units may directly face each other or be placed at a predetermined distance apart.

With regard to the suturing thread for face lift and body lift, if the vertices or bottom surfaces of the protrusions or protrusion units are placed at a distance apart, thickness of the connecting part between the vertices or bottom surfaces may be the same or higher than the thickness of a main thread of the suturing thread.

With regard to the suturing thread for face lift and body lift, if the vertices or bottom surfaces of the protrusions or protrusion units are placed at a distance apart, the distance between the vertices or bottom surfaces may be either regular or irregular.

With regard to the suturing thread for face lift and body lift, one protrusion pair or protrusion unit may play the role of an anchoring point.

With regard to the suturing thread for face lift and body lift, the protrusion pair or protrusion unit may be arranged either regularly or irregularly.

With regard to the suturing thread for face lift and body lift, the protrusion pair or protrusion unit may have several different units as a combination of protrusions having different shape.

With regard to the suturing thread for face lift and body lift, the protrusion pair or protrusion unit and a cog may be arranged either regularly or irregularly.

The suturing thread for face lift and body lift according to one example of the present invention can be produced by injection molding using a mold, cutting process using a lathe, variable extrusion molding using an extruder provided with variable nozzle, or heating-compression solid phase molding in which molding is carried out at temperature condition that the temperature is between the glass transition temperature and melting point, but the suturing thread is preferably produced by a variable cross-section extrusion process using a variable cross-section extruder provided with variable nozzle.

MODES FOR CARRYING OUT THE INVENTION

Hereinbelow, the examples of the present invention are explained in view of the drawings which briefly illustrate the ideal examples of the present invention. With regard to the drawings, modifications of illustrated configurations are expected depending on techniques for production and/or tolerance, for example. Accordingly, the examples under the technical idea of the present invention shall not be interpreted so as to be limited to specific configurations that are illustrated in the present specification, and they shall encompass the modifications of configurations which occur in due course of production, for example.

Furthermore, in the attached drawings, shape of the protrusion is basically illustrated by having a cone-shaped protrusion or a conical funnel-shaped protrusion as basic form. However, those protrusions can be replaced with protrusions having truncated cone, cylinder, polygonal cone, or truncated polygonal cone shape, and as those three-dimensional figures can be modified to various shapes, even when it is illustrated as a cone-shaped protrusion in the drawings to aid understanding of the present invention, it shall be simply explained as a protrusion.

FIG. 1 is a schematic drawing briefly illustrating the structure of the suturing thread for face lift and body lift according to one example of the present invention.

As illustrated in FIG. 1, with regard to suturing thread (10) according to one example of the present invention, protrusion (12) is formed at a predetermined interval on main thread (11) of a suturing thread. Protrusion (12) is produced integrally with main thread (11) of a suturing thread during production, and various methods can be employed for the production of suturing thread (10). As for the method, injection molding using a mold and variable cross-section extrusion molding using a variable cross-section extruder provided with variable nozzle are included. Optionally, it is possible that the suturing thread according to one example of the present invention is produced first in thicker basic thread form and then subjected to a cutting process which uses a lathe to form a cone-shaped protrusion. Incidentally, fixed surface (13) corresponding to the bottom surface of a cone can be a flat surface, or it can be a curved surface having a concave depression such that protrusion (12) may optionally play the role of a barb (not illustrated).

The expression "main thread of a suturing thread" as used herein means a main body of a suturing thread having long cylinder shape from which protrusion parts have been removed. It is described for the sake of convenience of identifying the structure of the suturing thread of the present invention, and it is not intended to indicate a separation type in which the main thread of a suturing thread is not integrated with protrusions.

Figure 2:
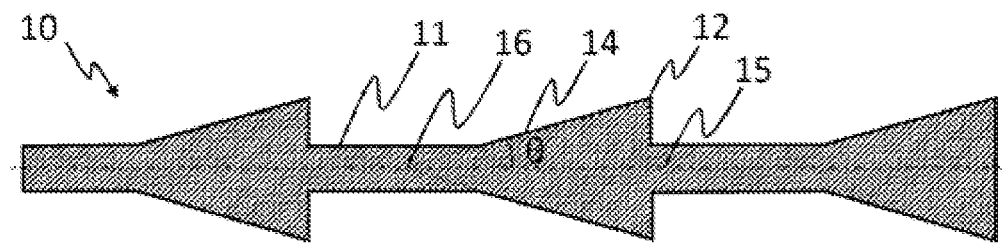
FIG. 2 is a cross-section drawing illustrating a cross-section of the suturing thread for face lift and body lift of FIG. 1 above.

FIG. 2 is a cross-section drawing illustrating a cross-section of the suturing thread for face lift and body lift of FIG. 1 above. As illustrated in FIG. 2, the cross-section of a protrusion part has a right triangle shape. In this case, the angle (θ) between generatrix (14) of the cone-shaped protrusion and center axis (15) of main thread (11) of a suturing thread is preferably 20° to 60°, because, if the angle is too large, poor procedural workability is yielded, and as the protrusion becomes excessively thin, there is a possibility that it is lost even before main thread (11) of a suturing thread. On the other hand, if the angle is too small, a poor fixing performance may be yielded as the area to be fixed on skin tissues is reduced. Meanwhile, the point at which extended generatrix lines of protrusions meet each other inside a main thread of the suturing thread is referred to as imaginary vertex (16).

Figure 3:
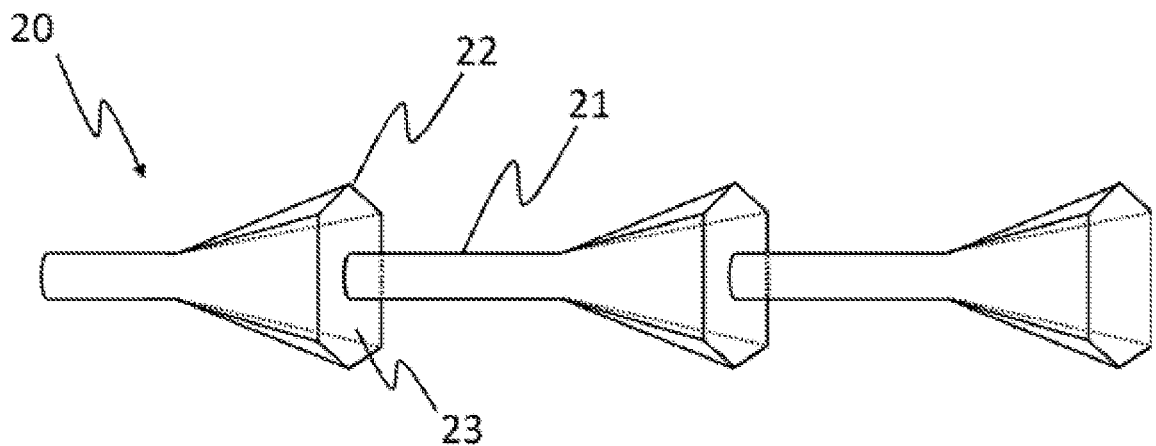
FIG. 3 is a schematic drawing briefly illustrating the structure of the suturing thread for face lift and body lift according to another example of FIG. 1 of the present invention.

FIG. 3 is a schematic drawing briefly illustrating the structure of the suturing thread (20) for face lift and body lift according to another example of FIG. 1 of the present invention. As illustrated in FIG. 3, a polygonal cone-shaped protrusion can be formed instead of a cone-shaped protrusion of FIG. 1. A polygonal cone has vertex (22) in the number of n and n-gonal bottom surface (23) composed of a line resulting from connection of the ends of generatrices. In FIG. 3, a hexagonal cone is illustrated as an example. However, a polygonal cone with any shape including a tetragonal cone, a pentagonal cone, and an octagonal cone can be used, and a modified polygonal cone having dents formed on the outer circumferential surface of a protrusion can be also used.

Figure 4:
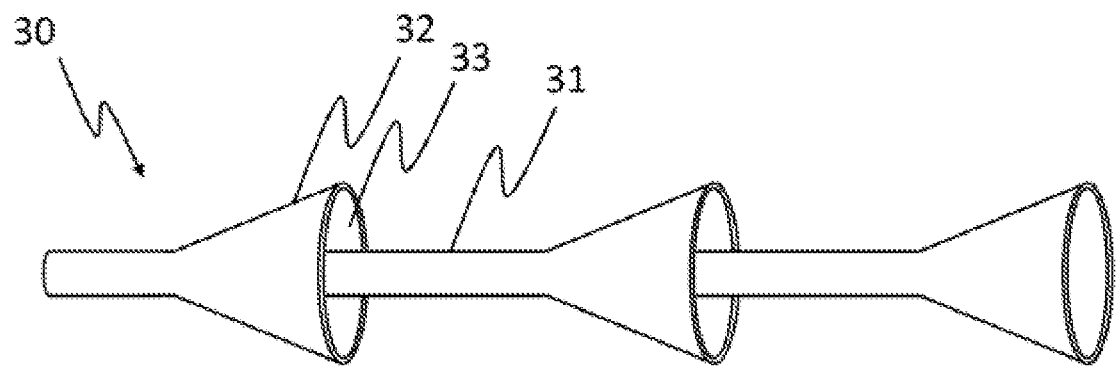
FIG. 4 is a schematic drawing briefly illustrating the structure of the suturing thread for face lift and body lift according to another example of the present invention.

FIG. 4 is a schematic drawing briefly illustrating the structure of the suturing thread (30) for face lift and body lift according to another example of the present invention. As illustrated in FIG. 4, funnel-shaped protrusion (32) may be formed on main thread (31) of the suturing thread. In that case, funnel wall (33) as an outer wall of funnel-shaped protrusion (32) preferably has a thickness that is 30% to 90% of the diameter of main thread (31) of the suturing thread. If the funnel wall is excessively thin, protrusions are degraded before skin is fixed so that a poor skin fixing effect may be yielded. On the other hand, if the funnel wall is excessively thick, it may be difficult to achieve favorable fixing.

Figure 5:
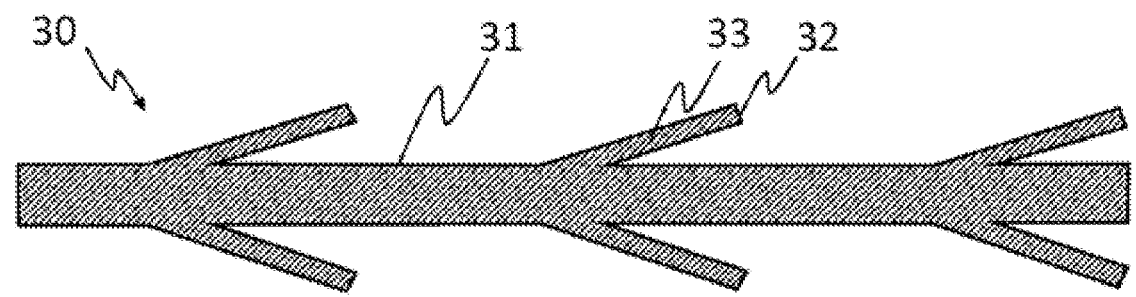
FIG. 5 is a cross-section drawing illustrating a cross-section of the suturing thread for face lift and body lift of FIG. 4 above.

FIG. 5 is a cross-section drawing illustrating a cross-section of the suturing thread for face lift and body lift of FIG. 4 above. As illustrated in FIG. 5, fixing of the suturing thread into a skin can be achieved by controlling the thickness of wall (33) of funnel-shaped protrusion (32).

Figure 6:
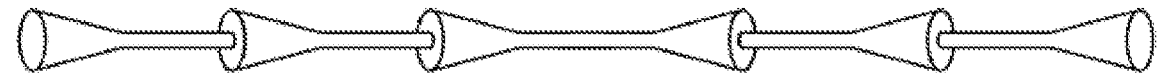
FIG. 6 is a schematic drawing briefly illustrating the structure of the suturing thread according to another example of the present invention, in which protrusions are formed in two directions.

FIG. 6 is a schematic drawing briefly illustrating the structure of the suturing thread according to another example of the present invention. As illustrated in FIG. 6, when it is assumed that the shape of a protrusion of the suturing thread for lift according to one example of the present invention has an arrow shape, protrusions can be formed in two directions such that the arrowheads lean toward the center part of the suturing thread (i.e., direction of the imaginary vertex leans toward the center part of the suturing thread). Namely, a plurality of protrusions can be symmetrically arranged around the center part of the suturing thread such that bottom surfaces of the plurality of protrusions lean toward the two ends of the suturing thread. When the arrowheads of a protrusion lean toward the center like FIG. 6, the protrusions play the role of applying tension on the suturing thread stretched in two directions. Namely, as the protrusions parts play the role of an anchor, the lifting effect of pulling from both points is exhibited.

Figure 7:
FIG. 7 is a schematic drawing briefly illustrating the structure of the suturing thread according to still another example of the present invention, in which protrusions are formed in two directions.

FIG. 7 is a schematic drawing briefly illustrating the structure of the suturing thread according to still another example of the present invention. Contrary to the one illustrated in FIG. 6, according to the suturing thread of still another example of the present invention, protrusions may be formed in symmetry form around the center part of the suturing thread such that arrowheads lean toward both ends (i.e., imaginary vertex leans toward both ends). In that case, instead of having a tension occurring from the two points at which the protrusions are fixed in opposite directions, the suturing thread is inserted in a state of having stretched skin tissue so that the anchoring effect of fixing the stretched skin is exhibited, and thus there is an advantage that skin tissues at specific area can be stretched. Namely, as illustrated in FIG. 7, a pair of protrusions having a bobbin shape itself can play the role of lifting and the role of an anchoring point simultaneously.

Figure 8:
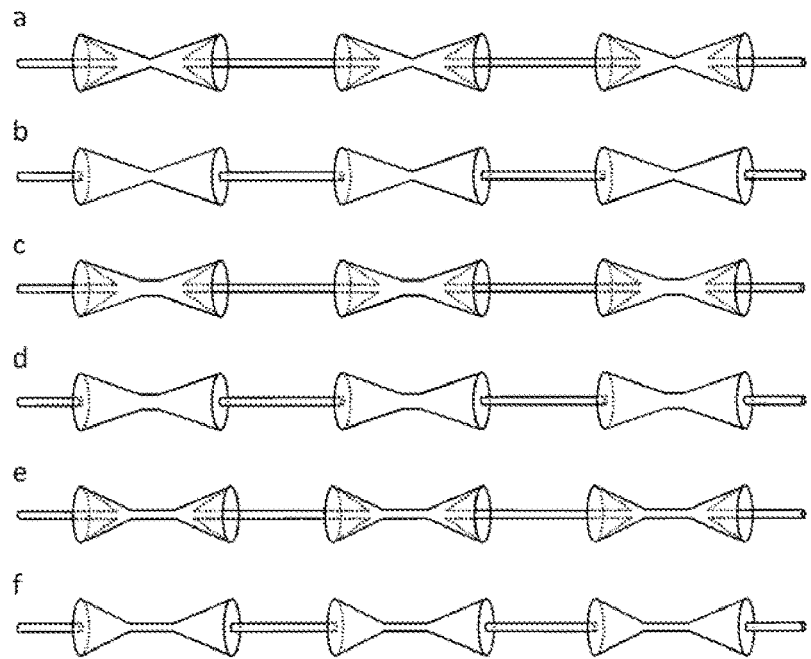
FIG. 8 is a schematic drawing briefly illustrating the structure of the suturing thread according to various examples of the present invention, in which a shows a structure of a suturing thread in which funnel-shaped protrusions are adhered while facing each other, b shows a structure of a suturing thread in which cone-shaped protrusions are adhered while facing each other, c shows a structure of a suturing thread in which thickness of the adhered part of the funnel-shaped protrusions of the above structure a is higher than the thickness of the main thread, d shows a structure of a suturing thread in which thickness of the adhered part of the cone-shaped protrusions of the above structure b is higher than the thickness of the main thread, e shows a structure of a suturing thread in which the funnel-shaped protrusions facing each other are not directly adhered but placed at a suitable distance apart, and f shows a structure of a suturing thread in which the cone-shaped protrusions facing each other are not directly adhered but placed at a suitable distance apart.

FIG. 8 is a schematic drawing briefly illustrating the structure of the suturing thread according to still another example of the present invention. When it is assumed that the protrusion has an arrow shape, protrusions can be formed such that a structure in which arrowheads face each other is repeatedly arranged. The two arrows may have the same size, or one arrow may be larger than the other. More specifically, as illustrated in a of FIG. 8, it is possible to have a structure of a suturing thread in which funnel-shaped protrusions are directly adhered while facing each other. Those adhered funnel-shaped protrusions are similar to a shape of a Jang-gu or a bobbin, and it is possible to have a structure in which the adhered funnel-shaped protrusions having a shape of a Jang-gu or a bobbin are repeatedly present. In that case, the adhered funnel-shaped protrusions may be replaced with adhered cone-shaped protrusions as shown in b of FIG. 8, or replaced with polygonal cone-shaped protrusions (not illustrated). Incidentally, the funnel-shaped protrusions, polygonal-shaped protrusions, or cone-shaped protrusions may be present at a predetermined distance apart via a connecting part, instead of being completely adhered to each other. Such structures are illustrated in c to f of FIG. 8. Specifically, c and e of FIG. 8 correspond to a suturing thread having funnel-shaped protrusions, and d and f of FIG. 8 correspond to a suturing thread having cone-shaped protrusions. In that case, the connecting part may be thicker than the main thread of a suturing thread (c and d of FIG. 8) or it may be the same as the main thread of a suturing thread (e and f of FIG. 8). If the connecting part is thick, it is possible to prevent breakage of a suturing thread at the connecting part on which the strongest tension is applied. The predetermined distance can be freely adjusted within a range in which it is ⅒ to 10 times the height of the cone-shaped protrusion or funnel-shaped protrusion. According to the suturing thread with a structure in which funnel-shaped protrusions, polygonal cone-shaped protrusions, or cone-shaped protrusions face each other to form a repeating bobbin structure as described above, two protrusions facing each other and a space therebetween pull tissues, thus exhibiting the lifting effect and simultaneously playing the role of anchoring point.

Figure 9:
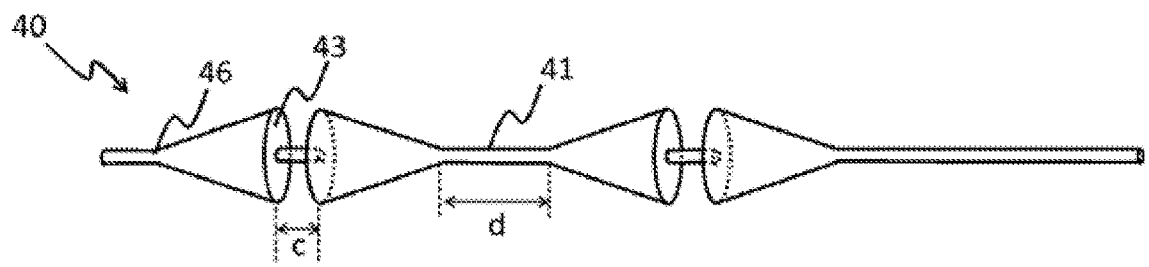
FIG. 9 is a schematic drawing briefly illustrating the suturing thread according to one example of the present invention, which has a shape in which bottom surfaces (43) of the protrusions face each other.

FIG. 9 is a schematic drawing briefly illustrating the suturing thread according to one example of the present invention, which has a shape in which bottom surfaces (43) of the protrusions face each other. Although distance c between bottom surfaces (43) facing each other is shorter than distance d between vertices (46) facing each other in FIG. 9, c and d may be the same or different from each other.

As illustrated in FIGS. 8 and 9, according to pulling of tissues by two protrusions facing each other and a space therebetween, the suturing thread for lift according to one example of the present invention exhibits the lifting effect and simultaneously plays the role of anchoring point.

Figure 10:
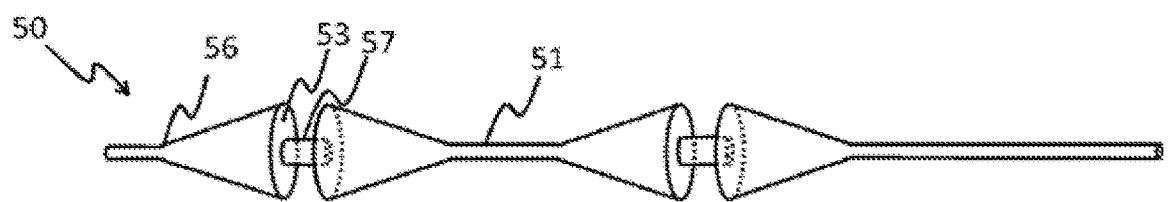
FIG. 10 is a schematic drawing briefly illustrating the suturing thread according to one example of the present invention, which has a shape in which bottom surfaces (53) of the protrusions face each other and the connecting line between bottom surfaces (53) of the protrusions has a thickness that is higher than the thickness of the main thread of a suturing thread.

FIG. 10 is a schematic drawing briefly illustrating the suturing thread according to one example of the present invention, which has a shape in which bottom surfaces (53) of the protrusions face each other and the connecting line between bottom surfaces (53) of the protrusions has a thickness that is higher than the thickness of the main thread of a suturing thread.

Figure 11:
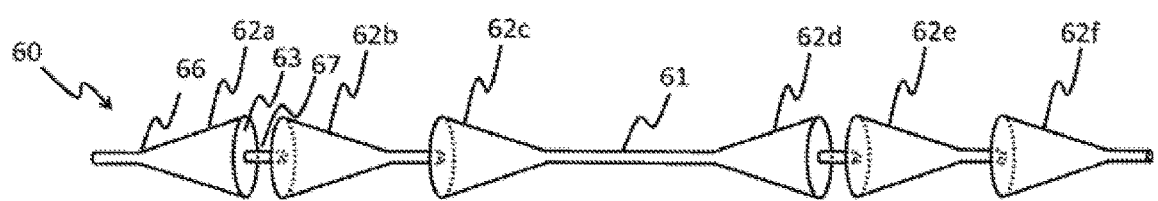
FIG. 11 is a schematic drawing briefly illustrating the suturing thread according to one example of the present invention, which has a shape in which one protrusion (62b) in one pair of protrusions, of which bottom surfaces (63) face each other, and a neighboring protrusion (62c) are formed in the same direction.

FIG. 11 is a schematic drawing briefly illustrating the suturing thread according to one example of the present invention, which has a shape in which one protrusion (62b) in one pair of protrusions, of which bottom surfaces (63) face each other, and a neighboring protrusion (62c) are formed in the same direction. Like two protrusions (62a, 62b) of which bottom surfaces (63) face each other and two protrusions (62b, 62c) leaning toward the same direction, order of arranging the protrusions may be irregular, and, in that case, length of suturing thread (67) between two protrusions (62a, 62b) of which bottom surfaces face each other and length of suturing thread between protrusions (62c, 62d) of which vertices face each other may be the same or different from each other. Furthermore, thickness of main thread (67) between protrusions (62a, 62b, 62d, 62e) of which bottom surfaces face one another may be the same or higher than the thickness of main thread (61) between vertices facing each other, and it may be the same or smaller than the thickness of bottom surface (63) of the protrusion.

Figure 12:
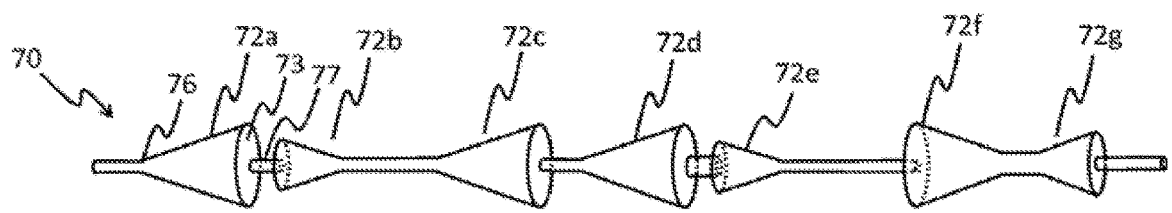
FIG. 12 is a schematic drawing briefly illustrating the suturing thread according to one example of the present invention, which has a shape in which one protrusion (72b) in one pair of protrusions, of which bottom surfaces face each other, has a smaller size than facing protrusion (72a).

FIG. 12 is a schematic drawing briefly illustrating the suturing thread according to one example of the present invention, which has a shape in which one protrusion (72b) in one pair of protrusions, of which bottom surfaces face each other, has a smaller size than facing protrusion (72a). When protrusions are regularly arranged like FIG. 8, or they are arranged in irregular directions like FIG. 11, size of continuous protrusions (72a, 72b, 72c, 72d, 72e, 72f, and 72g) may be the same or different from one another. In that case, the distance between protrusions may be also the same or different from one another.

Figure 13:
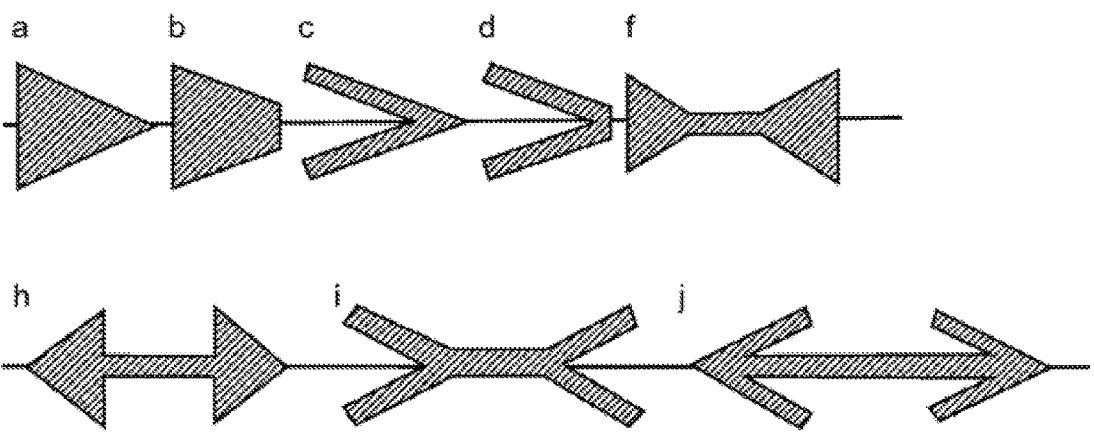
FIG. 13 is a longitudinal section drawing illustrating the longitudinal section of the protrusions having various outer profiles of the suturing thread according to one example of the present invention.

FIG. 13 is a longitudinal section drawing illustrating the longitudinal section of the protrusions having various outer profiles of the suturing thread according to one example of the present invention.

a is a longitudinal section that can be obtained when the protrusion has a cone shape or a polygonal cone shape, b is a longitudinal section that can be obtained when the protrusion has a truncated cone shape or a truncated polygonal cone shape, c is a longitudinal section that can be obtained when only the wall and main thread of the protrusion with a shape of cone or polygonal cone remain while the inside of the protrusion is empty to have a funnel shape, d is a longitudinal section that can be obtained when only the wall and main thread of the protrusion with a shape of truncated cone or truncated polygonal cone remain while the inside of the protrusion is empty to have a funnel shape, and f is a longitudinal section that can be obtained when two protrusions face each other to form protrusions having Jang-gu shape.

The aforementioned longitudinal sections of protrusions may exhibit various shapes depending on the shape of various protrusions that are explained in detail, and protrusions having those shapes may be arranged either regularly or irregularly.

Figure 14:
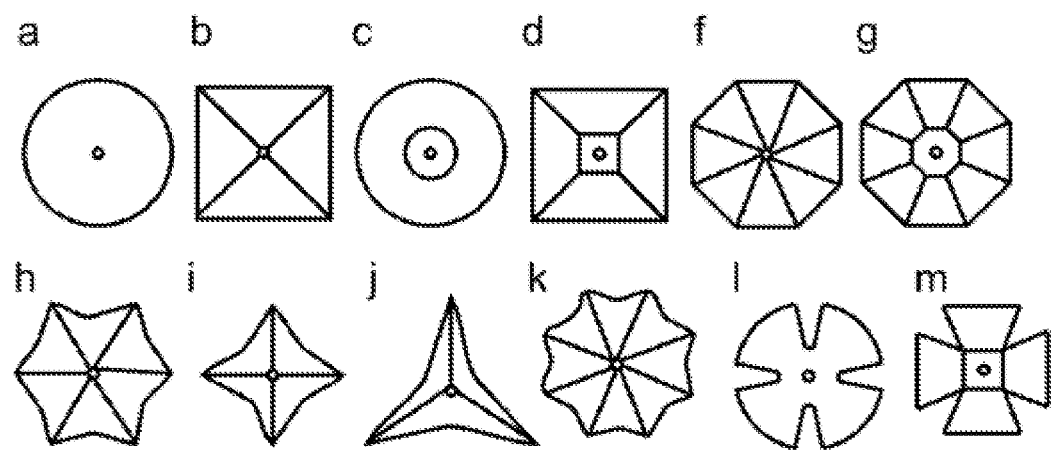
FIG. 14 is a lateral drawing illustrating protrusions having various outer profiles of the suturing thread according to one example of the present invention, in which the protrusions are viewed while having the suturing thread at the center.

FIG. 14 is a lateral drawing illustrating protrusions having various outer profiles of the suturing thread according to one example of the present invention, in which the protrusions are viewed while having the suturing thread at the center. Examples of the shape of the protrusion include cone (a), tetragonal cone (b), truncated cone (c), truncated tetragonal cone (d), octagonal cone (f), truncated octagonal cone (g), modified hexagonal cone (h) of which outer circumferential surface has a concave depression, modified tetragonal cone (i), modified trigonal cone (j), and modified octagonal cone (k), shape (1) in which a dent is formed on the wall of a funnel-shaped protrusion with cone shape, and shape (m) in which a dent is formed on the wall of a funnel-shaped protrusion with truncated tetragonal cone shape, and it is possible to have various modifications that are not illustrated.

Figure 15:
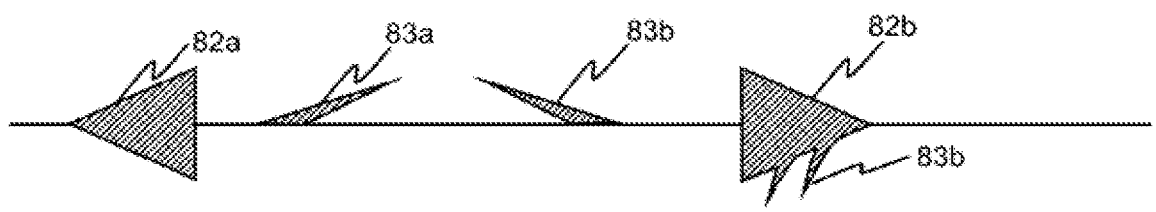
FIG. 15 is a schematic drawing briefly illustrating the suturing thread according to one example of the present invention, in which various modifications of a protrusion have been reflected.

FIG. 15 is a schematic drawing briefly illustrating the suturing thread according to one example of the present invention, in which various modifications of a protrusion have been reflected. As illustrated in FIG. 15, the aforementioned protrusions and cogs (cog 83*a*, 83*b*, and 83*c*) that are formed on a protrusion or a main thread may be arranged either regularly or irregularly.

The present invention has been explained in view of the examples that are given above. However, those examples are mere exemplifications and a person having general knowledge in the relevant art would understand that various modifications and other equivalent examples can be made from them. Accordingly, the true technical scope of the present invention for which protection is sought shall be determined based on the technical idea of the attached claims.

INDUSTRIAL APPLICABILITY

The suturing thread for face lift or body lift according to one example of the present invention can be used as a medical supply which is used for a medical procedure for improving health or skin beauty.

The invention claimed is:

1. A suturing thread for face lift and body lift made of a polymer or gold with a plurality of protrusion units formed on an outer circumferential surface of a main thread of the suturing thread in which each of the plurality of protrusion units consists of two protrusions and each protrusion of each protrusion unit has a structure of cone, polygonal cone, truncated cone, modified polygonal cone, truncated polygonal cone, or modified truncated polygonal cone formed to have a radially symmetric structure around the main thread of the suturing thread, or has a funnel shape in which a part or whole of a space defined by a circumferential surface of the structure and the main thread of the suturing thread is empty, and the two protrusions of each protrusion unit are directly adhered to each other in an hourglass-shaped arrangement so as to form a unitary protrusion unit structure in which an imaginary vertex of one protrusion of the protrusion unit structure is oriented in a direction opposite that of an imaginary vertex of another protrusion of the protrusion unit structure.

2. The suturing thread for face lift and body lift according to claim 1, wherein an angle of a generatrix as a slope of the protrusion structure is formed at an angle of 20° to 60° relative to a center axis of the main thread of the suturing thread.

3. The suturing thread for face lift and body lift according to claim 1, wherein a bottom surface of the protrusion structure is either a flat surface or a curved surface which is concavely depressed.

4. The suturing thread for face lift and body lift according to claim 1, wherein thickness of an outer wall of the funnel shape is 30% to 90% of the diameter of the main thread of the suturing thread.

5. The suturing thread for face lift and body lift according to claim 1, wherein the polymer is either a non-absorbable polymer or an absorbable polymer.

6. The suturing thread for face lift and body lift of claim 5, wherein the non-absorbable polymer is selected from the group consisting of PET (polyenthylene terephthalate), nylon, polyamide, PVDF (polyvinyldene fluoride), and polypropylene.

7. The suturing thread for face lift and body lift of claim 5, wherein the absorbable polymer is selected from the group consisting of polydioxanone, polymer of lactic acid (L-lactide), polymer of glycolic acid (glycolide), copolymer of lactic acid and glycolic acid (glycolide) or poly dioxane, lactic acid (L-lactide), glycolic acid (glycolide), or a copolymer thereof blended with caplolactone or trimethylene carbonate.

8. The suturing thread for face lift and body lift according to claim 1, wherein the plurality of protrusion units is formed by alternately arranging protrusions in one direction and protrusions in an opposite direction.

9. The suturing thread for face lift and body lift according to claim 8, wherein the suturing thread is a symmetry type in which a number of the protrusions arranged in one direction is the same as a number of the protrusions arranged in the opposite direction.

10. The suturing thread for face lift and body lift according to claim 1, wherein the two protrusions of each protrusion unit are formed in two directions such that extended generatrix lines of the protrusions meet each other inside the main thread of the suturing thread, the imaginary vertices of the protrusion unit structures defining an angle oriented in each of the two directions.

11. The suturing thread for face lift and body lift according to claim 1, wherein the plurality of protrusion units comprise protrusions of a same size or of different sizes.

12. The suturing thread for face lift and body lift according to claim 1, wherein the plurality of protrusion units comprise protrusions of a same shape or of different shapes.

13. The suturing thread for face lift and body lift according to claim 1, wherein the plurality of protrusion units is arranged either regularly or irregularly.

14. The suturing thread for face lift and body lift of claim 1, wherein a bottom surface of each of the protrusions is of a circular shape, an oval shape, a polygonal shape, or a modified polygonal shape.

15. The suturing thread for face lift and body lift of claim 1, wherein extended generatrix lines defining the imaginary vertex of the one protrusion of the protrusion unit structure overlap extended generatrix lines defining the imaginary vertex of the other protrusion of the protrusion unit structure.

* * * * *